United States Patent
Giuliani et al.

(10) Patent No.: US 8,476,276 B2
(45) Date of Patent: Jul. 2, 2013

(54) PHARMACEUTICAL COMPOSITIONS BASED ON KININ B2 RECEPTOR ANTAGONISTS AND CORTICOSTEROIDS, AND THEIR USE

(75) Inventors: Sandro Giuliani, Bagno A Ripoli (IT); Carlo Alberto Maggi, Florence (IT)

(73) Assignee: Istituto Luso Farmaco d'Italia S.p.A., Peschiera Borromeo (IT)

( * ) Notice: Subject to any disclaimer, the term of this patent is extended or adjusted under 35 U.S.C. 154(b) by 177 days.

(21) Appl. No.: 13/003,608

(22) PCT Filed: Jul. 3, 2009

(86) PCT No.: PCT/EP2009/004847
§ 371 (c)(1),
(2), (4) Date: Jan. 11, 2011

(87) PCT Pub. No.: WO2010/003601
PCT Pub. Date: Jan. 14, 2010

(65) Prior Publication Data
US 2011/0112011 A1   May 12, 2011

(30) Foreign Application Priority Data
Jul. 11, 2008   (IT) .............................. MI2008A1264

(51) Int. Cl.
*A61K 31/4709*   (2006.01)
*A61K 31/47*   (2006.01)
*C07D 405/12*   (2006.01)
*C07D 215/26*   (2006.01)

(52) U.S. Cl.
USPC ..................................... 514/253.06; 544/363

(58) Field of Classification Search
None
See application file for complete search history.

(56) References Cited

FOREIGN PATENT DOCUMENTS

| EP | 1 894 559 | 3/2008 |
|----|-----------|--------|
| WO | 03/000696 | 1/2003 |
| WO | 2004/069266 | 8/2004 |
| WO | 2006/040004 | 4/2006 |
| WO | 2007/003411 | 1/2007 |

OTHER PUBLICATIONS

Barnes ("Efficacy of inhaled corticosteroids in asthma," Current reviews of allergy and clinical immunology, 1998, vol. 102, p. 531-538).*
UW Orthopaedics and Sports Medicine ("Corticosteroids for Arthritis" published online Dec. 30, 2004).*
Sharma, J. et al., "Inhibition of rats adjuvant arthritis by a bradykinin antagonist Hoe 140 ans its influence on kallikreins" General Pharmacology, 27(1), 1996 pp. 133-136.
Rejean Couture, et al., Kinin Receptors in Pain and Inflammation, European Journal of Pharmacology, 429, pp. 161-176, 2001.
Chien-Da Huang, et al., Bradykinin Induces Interleukin-6 Production . . . , Am. J. Respir. Cell Nol. Biol., vol. 28, pp. 330-338, 2003.

* cited by examiner

*Primary Examiner* — Christina Bradley
(74) *Attorney, Agent, or Firm* — Lucas & Mercanti, LLP

(57) ABSTRACT

Disclosed are pharmaceutical compositions containing, as active ingredients, a mixture of a corticosteroid and a kinin B2 receptor antagonist. Said compositions have proved particularly effective, especially in the treatment of inflammatory disorders such as asthma, ophthalmic or dermatological disorders and, above all, as regards the joints, arthritis.

18 Claims, No Drawings

PHARMACEUTICAL COMPOSITIONS BASED ON KININ B2 RECEPTOR ANTAGONISTS AND CORTICOSTEROIDS, AND THEIR USE

This application is a U.S. national stage of PCT/EP2009/004847 filed on Jul. 3, 2009 which claims priority to and the benefit of Italian Application No. MI2008A001264 filed on Jul. 11, 2008, the contents of which are incorporated herein by reference.

FIELD OF INVENTION

Disclosed are pharmaceutical compositions containing, as active ingredients, a mixture of a corticosteroid and a kinin B2 receptor antagonist. Said compositions have proved particularly effective, especially in the treatment of inflammatory disorders such as asthma, ophthalmic or dermatological disorders and, above all, as regards the joints, arthritis.

STATE OF THE ART

Osteoarthritis (OA), also known as degenerative joint disease, is a painful, progressive, degenerative disorder of the joints. The main pathophysiological characteristics of OA are destruction and loss of joint cartilage, hypertrophy, inflammation of the synovial membrane, and consequent swelling of the joint. These effects produce symptoms such as pain, stiffness and loss of function. The high incidence of OA in the elderly population, associated with the increase in average life expectancy, indicates that the number of patients affected by this disorder is likely to increase considerably in the near future. OA patients consider pain reduction to be very important to their quality of life.

No drugs which stop the progression of this disorder are currently available. The existing treatments are mainly designed to reduce the pain symptoms and regain the joint function. Paracetamol and non-steroidal anti-inflammatory drugs (NSAIDs) are widely prescribed for the treatment of pain in osteoarthritis. However, long-term use of said drugs can be accompanied by major adverse effects, especially at gastrointestinal level (ulcers) and in terms of platelet aggregation.

Bradykinin (BK) is a member of the kinins, a family of small peptides (8-11 aminoacids) which derive from precursors with a high molecular weight (kininogens) following attack by enzymes with peptidase activity (kallikreins). Kinin formation is activated in various circumstances, involving inflammatory, ischaemic and immune processes or bacterial and viral infections.

Two kinin receptors have been pharmacologically characterised: the B1 receptor, which is minimally expressed under normal conditions, but whose expression is induced by the stimuli listed above, and the B2 receptor, which is constitutionally expressed by many cell types. Bradykinin, through stimulation of the B2 receptor, is one of the most important mediators of inflammation and pain, and is involved in the release of pro-inflammatory and hyperalgesic mediators.

It has been demonstrated that bradykinin (BK) participates in the pathophysiology of OA at various levels.

It has long been known that kinins are released into the synovial fluid of OA sufferers. Moreover, in these patients, the B2 receptor has been found in the cells lining the synovial cavity, the fibroblasts, and the endothelial cells of the blood vessels.

Many studies with various preclinical models indicate that BK, when administered by the intra-articular route, induces plasma extravasation and accumulation of neutrophils in the synovia of the rat more effectively than other inflammation mediators such as substance P, histamine, and calcitonin gene-related peptide. Moreover, BK reduces the proteoglycans content in the joint cartilage and generates the release of prostaglandins in murine OA models.

Some bradykinin B2 receptor antagonists have proved effective in inhibiting inflammatory events and hyperalgesia in various animal synovitis models.

After its release, BK excites and sensitises the sensory nerve fibres that innervate the articular capsule.

The clinical significance of BK has been demonstrated in a phase II trial conducted on 58 patients with symptomatic OA of the knee, in which a single intra-articular administration of B2 receptor antagonist icatibant (90 µg/1 ml) reduced the intensity of pain in the knee to a greater extent than the placebo (55 patients). Sanofi-Aventis recently reported that in patients with OA of the knee, intra-articular infiltration of icatibant (3×500 µg injections one week apart) induces a strong analgesic response which lasts for up to 3 months after the treatment, and this considerable analgesic effect is obtained with negligible or no side effects.

Kinins are potent inflammatory agents in the airways and elsewhere. Local application of bradykinin or endogenously released kinins in the airways produces inflammatory effects and bronchoconstriction in asthma patients, but few effects in healthy volunteers. Kinin antagonists, especially kinin B2 receptor antagonists, can be useful in the treatment of allergic asthma.

Many bradykinin B2 receptor antagonists have been described in the literature: Steward, J. M. et al *Immunopharmacology*, 1999, 43, 155-61 (compounds B10056, B9430).

Pruneau, D et al. *Br. J. Pharmacol* 1998, 125, 365-72 (compounds FR167344, FR173657, LF160687, Bradizide, LF160335).

EP370453 describes some compounds with a peptide structure which act as bradykinin antagonists, and said compounds include the one defined as icatibant. Icatibant also forms the subject of patent EP1594520, wherein its use in the prophylaxis and treatment of osteoarthritis is disclosed.

WO03103671 describes a group of very powerful non-peptide bradykinin antagonists. A selection of particularly potent antagonists is reported in WO2006040004, including the compound MEN16132; also these antagonists have proved highly effective in the prophylaxis and treatment of osteoarthritis, especially in intra-articular treatments of the knee.

Natural cortisones (glucocorticoids or corticosteroids), cortisone and cortisol, are produced in the adrenal cortex, and have a steroidal molecular structure.

Their anti-inflammatory and antiallergic action is mainly produced by inducing synthesis of the enzyme lipocortin, which inhibits phospholipase A2. This enzyme converts membrane phospholipids into arachidonic acid which, in turn, via the enzymes cyclooxygenase and lipoxygenase, is converted to inflammation mediators such as prostaglandins and leucotrienes. Moreover, the cortisones interfere with the synthesis of proteins and enzymes, and stabilise the cell membranes.

Corticosteroids inhibit the inflammatory response, whether the stimulating agent that produced it was chemical, infectious or immunological. Although cortisone administration has the characteristics of symptomatic treatment, because cortisones do not act on the causes of the disorder, suppression of inflammation and its consequences makes these agents very useful in clinical practice. Cortisones inhibit not only the early symptoms of the inflammatory process (oedema, and alteration of the haematic and lymphatic microcirculation) but also subsequent symptoms such as redness and pain.

Synthetic corticosteroids, which are derived from cholic acid, differ slightly from natural corticosteroids; the modifications introduced are designed to increase the half-life of the substances, leaving the biochemical activities of the natural compounds unchanged.

Cortisones are generally little used by the oral route in degenerative or inflammatory osteoarticular disorders, due to their low efficacy and potentially serious systemic side effects that emerge in particular in long-term treatments, which are often necessary in chronic inflammatory disorders.

Administration by local infiltration has become increasingly important in recent years in the treatment of osteoarticular and osteomuscular disorders. This treatment procedure is indicated in acute inflammatory processes associated with pain and functional limitation, and in degenerative joint diseases such as osteoarthritis, non-infective arthritis, tendinitis, bursitis, fascitis, fibromyalgia and radicular syndromes.

The purpose of infiltration with cortisones is to reduce or eliminate the articular or periarticular inflammation and prevent systemic diffusion. Microcrystalline suspensions with a long dissolution time, which prolong the duration of action, are used for this purpose. The presence of microcrystals introduced into the joint can cause post-infiltration pain; they are consequently co-administered with local anaesthetics to reduce the pain. Patients are advised to rest the joint for at least 24 hours to prevent systemic absorption of the drug. High doses of cortisones, even if applied locally, must be avoided to prevent systemic absorption, which is contraindicated in a series of common disorders such as ulcers, diabetes, heart failure, osteoporosis and hypertension.

For intra-articular or intrabursal administration and injection into the tendon sheaths and tendon cyst formations, the dose of cortisones is consequently evaluated at the time, depending on the severity of the symptoms and the size of the joint or other local area to be treated (the doses generally range between 1 and 100 mg). In evolving forms with polyarticular symptoms high doses are administered, sometimes by single injections performed at different sites simultaneously.

In any event, the numerous adverse effects of cortisones, at both systemic and local level, have led to a search for alternative solutions designed to reduce the dose or use of cortisones.

The anti-inflammatory and analgesic activity of both classes of compound ($B_2$ receptor antagonists and cortisones) is well known in the scientific literature. According to the state of the art, it would be entirely reasonable to consider that both cortisones and bradykinin B2 receptor antagonists produce antinociceptive and anti-inflammatory effects with similar mechanisms. In particular, both inhibit prostaglandin synthesis as well as having inhibitory effects on the synthesis of other pro-inflammatory compounds (cytokines). On the basis of these factors, it is not foreseeable that the two classes of compound would have an additive effect when administered together. However, our experimental observations have demonstrated not only an additive effect but also an unexpected synergy between bradykinin B2 receptor antagonists and cortisones, with a marked boosting effect in inhibiting the inflammatory and algogenic response in the models studied, and this finding constitutes the crux of this invention.

It is also well known that synthetic corticosteroids, especially after repeated, long-term administration, cause serious side effects and are contraindicated in a number of disorders, as stated above, because they can worsen them. Moreover, as demonstrated, for example, in pre-clinical studies with experimental knee osteoarthritis models, the effect of cortisones is partial and does not resolve more than 50% of the parameters altered by the inflammatory process such as pain, increase in pro-inflammatory cells and oedema.

A formulation containing cortisones which completely inhibits inflammation at lower doses would consequently be desirable from the therapeutic standpoint.

An unexpected and surprising activity deriving from the association of kinin $B_2$ receptor antagonists and corticosteroids in reducing inflammatory processes has now been found. This activity can be very useful in various disorders such as osteoarthritis, rheumatoid arthritis, asthma, COPD, or inflammatory ophthalmological and dermatological disorders, with a substantial additive and synergic effect of the two classes of compound.

For example, in osteoarthritis of the knee, the association of $B_2$ antagonists and cortisones produces 1) a complete anti-inflammatory therapeutic effect, 2) longer-lasting effects, and 3) up to a ten-fold reduction in the dose of corticosteroid.

This unexpected additive property, and above all the mutual boosting of the two classes of compound, applies to all the other forms of inflammation in which kinins play an important part, such as asthma, in which the efficacy of corticosteroids is well known. The possibility of obtaining significant effects with a lower quantity of corticosteroid is an important and innovative prospect in the treatment of inflammatory processes in general.

DETAILED DESCRIPTION

It has now surprisingly been found that the use of natural or synthetic cortisones administered in association with kinin B2 receptor antagonists is surprisingly effective in the treatment of inflammatory disorders, such as, but not limited to, osteoarthritis and degenerative joint disease, arthritis, rheumatoid arthritis, asthma and COPD, ophthalmological and dermatological disorders.

This invention relates to pharmaceutical compositions containing, as active ingredients:
a) a natural or synthetic corticosteroid
b) a kinin B2 receptor antagonist
together with pharmaceutically acceptable vehicles and excipients, and the use of said active ingredients to prepare said compositions.

Said active ingredients can be administered not only in compositions wherein the two active ingredients are present simultaneously, but also in separate forms by simultaneous or sequential administration wherein treatment with the composition containing the kinin B2 receptor antagonist can precede or follow treatment with the composition containing the corticosteroid, with an interval between the two treatments ranging between 1 minute and up to 8 hours, preferably between 1 and 30 minutes.

Among the corticosteroids, particularly preferred are:
Cortisone, Hydrocortisone, Beclomethasone, Betamethasone, Budesonide, Dexamethasone, Flumethasone, Flunisolide, Fluocortone, Fluticasone, Methylprednisolone, Methylprednisone, Paramethasone, Prednisolone, Triamcinolone,
as they are or in the form of an ester with acetic, benzoic, caproic, succinic, phosphoric, propionic or valeric acid, or in the form of acetonides;

The B2 kinin receptor antagonists can be selected from the group consisting of:

H-D-Arg-Arg-Pro-Hyp-Gly-Igl-Ser-D-F5F-Igl-Arg-OH (B10056),

H-Arg-Arg-Pro-Hyp-Gly-Igl-Ser-D-Igl-Oic-Arg-OH (B9430),

H-D-Arg-Arg-Pro-Hyp-Gly-Thi-Ser-D-Tic-Oic-Arg-OH (Icatibant),

4-[2-[([[3-(3-Brom-2-methyl-imidazo[1,2-a]pyridine-8-yl oxymethyl)-2,4-dichloro-phenyl]-methyl-carbamoyl]-methyl)-carbamoyl]-vinyl]-N,N-dimethyl-benzamide, (FR 167344)

3-(6-Acetylamino-pyridin-3-yl)-N-([[2,4-dichloro-3-(2-methyl-quinolin-8-yloxymethyl)-phenyl]-methyl-carbamoyl]-methyl)-acrylamide, (FR173657 op.FK3657)

1-[2,4-Dichloro-3-(2,4-dimethyl-quinolin-8-yloxymethyl)-benzene sulfonyl]-pyrrolidine-2-carboxylic acid [3-(4-carbamidoyl-benzoylamino)-propyl]-amide, (LF160687, Anatibant)

Bradizide, 4-(4-[1-[2,4-Dichloro-3-(2,4-dimethyl-quinolin-8-yloxymethyl)-benzenesulfonyl]-pyrrolidine-2-carbonyl]-piperazine-1-carbonyl)-benzamidine, (LF160335)

2-[5-(4-Cyano-benzoyl)-1-methyl-1H-pyrrol-2-yl]-N-[2,4-dichloro-3-(2-methyl-quinolin-8-yl oxymethyl)-phenyl]-N-methyl-acetamide, or one of the compounds disclosed in WO2006/04004, having general formula (I)

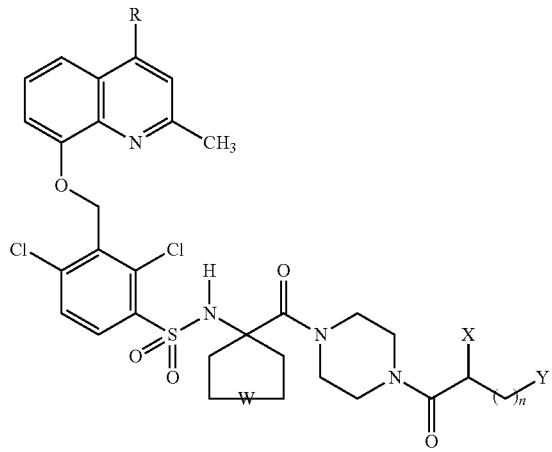

wherein

R is hydrogen or methyl;

W represents a single bond or an oxygen atom;

n=3, 4;

X is hydrogen or an amine group —NR1R2 wherein R1 and R2 are, independently from one another, hydrogen or a group selected from methyl, ethyl, n-propyl, isopropyl;

Y is a quaternary ammonium —NR3R4R5 wherein R3, R4, R5, independently from one another, are methyl, ethyl, n-propyl, isopropyl, butyl, isobutyl, n-pentyl;

and A⁻ an anion formally derived from a pharmaceutically acceptable acid;

and the pharmaceutically acceptable salts, enantiomers and enantiomeric mixtures thereof.

For the purposes of this invention, a pharmaceutically acceptable acid is an acid selected from hydrochloric, hydrobromic, phosphoric, carbonic, acetic, sulphuric, trifluoroacetic, methansulphuric, succinic, maleic, malic, malonic, citric, edetic acid; where the anion carries two or more negative charges, A⁻ shall be a fractional value.

This invention specifically relates to pharmaceutical compositions wherein the kinin $B_2$ receptor antagonist is selected from:

icatibant or a compound with general formula (I).

Of the compounds with general formula (I), the following compound is particularly preferred: (4-(S)-amino-5-(4-{4-[2,4-dichloro-3-(2,4-dimethyl-quinolin-8-yloxymethyl)-benzenesulphonylamino]-tetrahydro-pyran-4-carbonyl}-piperazin-1-yl)-5-oxo-pentyl]-trimethyl-ammonium, in salified form with ions formally deriving from an acid selected from hydrochloric, acetic, sulphuric, trifluoroacetic, methanesulphonic, succinic and edetic acids; chloride bi-hydrochloride is the compound defined as MEN16132 (MW 871.5).

wherein the amount of B2 kinin receptor antagonist per single dosage unit ranges from $6 \times 10^{-5}$ to $2 \times 10^{-2}$, preferably from $1 \times 10^{-4}$ to $1 \times 10^{-2}$, more preferably from $3 \times 10^{-4}$ to $6 \times 10^{-3}$ millimoles, corresponding to an amount of MEN16132 ranging from 0.05 to 17, from 0.09 to 9 and from 0.26 to 5 mg per single unit dosage, respectively.

The compositions according to the invention contain a quantity of bradykinin antagonist per dose of between $6 \times 10^{-5}$ and $2 \times 10^{-2}$ millimoles (in the case of MEN16132 they correspond to an approx. quantity of 0.05 to 17 mg), preferably between $1 \times 10^{-4}$ and $1 \times 10^{-2}$ millimoles (in the case of MEN16132 they correspond to an approx. quantity of 0.09 to 9 mg) and even more preferably between $3 \times 10^{-4}$ and $6 \times 10^{-3}$ millimoles (in the case of MEN16132 they correspond to an approx. quantity of 0.26 to 5 mg).

Moreover, said compositions contain a corticosteroid in the quantity of 0.05 to 100 mg, preferably 0.1 to 10 mg, per dose.

Pharmaceutical formulations according to this invention can also contain one or more pharmaceutically acceptable carriers/excipients.

Liquid and semisolid pharmaceutical forms suitable for topical administration, such as solutions, creams, gels or transdermal patches, are preferred; in particular, forms suitable for intra-articular or intrabursal injection, such as solutions, and transdermal application, such as semisolid forms like creams or gels and transdermal patches. The pharmaceutical form can also consist of a form wherein some or all of the components are in a dry form, possibly lyophilised, to be reconstituted with an aqueous solution or other suitable vehicle before use.

Said formulations can be produced by methods well-known in the state of the art using known excipients such as binders, disintegrants, fillers, stabilisers, diluents and colorants. They can also include delayed- or slow-release forms made with suitable polymers known in pharmaceutical technology.

Pharmaceutically acceptable carriers/excipients such as solvents, preservatives such as antioxidants and/or chelating agents and antimicrobials, isotonicity regulators, and buffer systems are preferred for the preparation of liquid forms suitable for injectable use.

Water is preferable as solvent, possibly with co-solvents such as glycols, or polyalcohols such as ethylene glycol.

Preservatives or chelating agents may also be used, sodium edetate and sodium metabisulphite being preferred, and antimicrobials, benzyl alcohol being preferred.

Sodium chloride or mannitol are particularly preferred as isotonicity regulators.

The preferred buffer systems can be the complex of salts for the phosphate and citrate buffer, preferably in the form of sodium or potassium salts.

In the preparation of liquid forms suitable for nebulisation, pharmaceutically acceptable vehicles/excipients are preferred as solvents, with preservatives such as antioxidants and/or chelating agents and antimicrobials, isotonicity regulators, and buffer systems.

In forms suitable for aerosol administration for application in the airways, pharmaceutically acceptable vehicles/excipients and propellants are preferred, preferably hydrofluorocarbons.

For nasal administration, dry powder forms administered with a suitable device or spray forms are preferred.

Typical examples of formulations according to the invention are:

1. Corticosteroid, 0.1-10 mg, MEN16132 0.26-5 mg, in saline solution (0.9% NaCl), 0.1N HCl q.s. to a pH of between 4.5 and 6, water q.s. to 1 ml.
2. Corticosteroid, 0.1-10 mg, MEN16132 0.26-5 mg, in saline solution (0.9% NaCl), buffer system for pH 6-8, water q.s. to 1 ml.
3. Extempore preparation obtained by dissolving 0.26-5 mg of lyophilised MEN16132 with 0.1-10 mg of a corticosteroid solution, with a buffer system in saline solution (0.9% NaCl), water q.s. to 1 ml.
4. Corticosteroid, 0.1-10 mg, icatibant (MW 1304.5) 0.39-7.8 mg, in saline solution (0.9% NaCl), buffer system at pH 6-8, water q.s. to 1 ml.

The pharmaceutical compositions according to the invention are useful in the prophylaxis and treatment of acute or chronic inflammatory, autoimmune, traumatic and degenerative disorders of the joints, such as: osteoarthritis and post-traumatic osteoarthritis, degenerative osteoarthritis (gonarthritis, spondylarthritis); spondylosis, synovitis, tenosynovitis, bursitis, contusions, sprains, dislocations and subluxations, attacks of gout.

Moreover, said compositions are useful in inflammatory disorders of the airways, especially asthma, rhinitis, chronic obstructive pulmonary disease (COPD), pulmonary fibrosis and disorders in which bronchial oedema or bronchospasm play a significant part; and in allergic and non-allergic inflammatory dermatological disorders and ophthalmic disorders deriving from chemical and physical agents or trauma. In dermatological disorders the main therapeutic indication is for dermatitis caused by burns (heat or sunburn), dermatitis or eczema caused by contact with allergenic or irritant substances, atopic dermatitis and autoimmune dermatitis (psoriasis), while in the case of ophthalmic disorders its main application is for blepharitis, conjunctivitis and blepharoconjunctivitis.

The dose can vary according to the patient's age and general state of health, the nature and severity of the disease or disorder, and the route and type of administration. In the case of intra-articular use in an adult human patient, the pharmaceutical compositions according to the invention could be administered as a weekly dose (in a single administration) of bradykinin antagonist amounting to between $3\times10^{-4}$ and $6\times10^{-3}$ mmols (in the case of MEN16132, this corresponds to approx. 0.26 to 5 mg) and between 0.1 and 10 mg of corticosteroid.

The following examples of compositions containing the two active ingredients illustrate the invention in greater detail:

Example 1

Betamethasone, 1 mg, MEN16132 0.5 mg, in saline solution (0.9% NaCl), 0.1 N HCl q.s. to pH 4.5, water q.s. to 1 ml. The solution is placed in pre-filled 2.25 ml syringes.

Example 2

Beclomethasone, 0.25 mg, MEN16132 0.5 mg, in saline solution (0.9% NaCl), containing phosphate buffer ($Na_2HPO_4$ 0.16 mg, $NaH_2PO_4$ 0.04 mg), water q.s. to 1 ml. The solution is placed in pre-filled 2.25 ml syringes.

Example 3

Betamethasone 1 mg, in saline solution (0.9% NaCl), containing phosphate buffer ($Na_2HPO_4$ 0.16 mg, $NaH_2PO_4$ 0.04 mg), water q.s. to 1 ml. MEN16132, in lyophilised form, is dissolved with the solution described above.

Example 4

Dexamethasone, 4 mg, icatibant 0.5 mg, in saline solution (0.9% NaCl), containing phosphate buffer ($Na_2HPO_4$ 0.16 mg, $NaH_2PO_4$ 0.04 mg), water q.s. to 1 ml. The solution is placed in pre-filled 2.25 ml syringes.

Example 5

A typical example of sequential administration of the two active ingredients involves the use of two compositions of the following type:

a) MEN16132 0.5 mg dissolved in an isotonic solution of NaCl (0.9% NaCl), 0.1N HCl to pH 5, EDTA 100 micromol/ml, isotonic solution q.s. to 2 ml, placed in syringes with a capacity of 2.25 ml; the dose is modulated by adjusting the volume administered by the intra-articular route (0.5 ml corresponds to 0.125 mg, 1 ml to 0.250 mg, 1.5 to 0.375 mg, and 2 ml to 0.500 mg). In the case of doses exceeding 0.5 mg, the contents of two syringes can be injected.

b) betamethasone disodium phosphate 1.97 mg dissolved in an isotonic solution of NaCl q.s. to 2 ml containing phenol, sodium edetate and sodium metabisulphite as stabilisers, placed in syringes with a capacity of 2.25 ml; the dose is modulated by adjusting the volume administered by the intra-articular route.

Biological Activity

The activity of MEN16132, icatibant and cortisones was measured in an experimental model of arthritis induced by intra-articular injection of carrageenan which causes a strong inflammatory effect.

Carrageenan (25 μl of a 2% solution) was injected into the intra-articular space of the right knee of the rat, while 25 μl of saline was administered to the left knee to provide an internal control.

The administration of carrageenan causes joint oedema, pain, difficulty of walking and inability to bear weight on the paw corresponding to the treated knee, with a peak effect 6 hours after administration; the weight of the body therefore falls mainly on the left paw to an extent directly proportional to the pain perceived in the right paw. The weight imbalance on the two weight-bearing paws, evaluated in a non-invasive way with the incapacitance test, measures the pain resulting from the joint inflammation. The diameter of the knee joint was also measured to measure the oedema.

The purpose of this trial was to evaluate the protective effect of kinin B2 receptor antagonists towards carrageenan-induced joint oedema and pain and to establish the effect produced by co-administration of a corticosteroid, specifically dexamethasone or hydrocortisone.

MEN16132 or icatibant (100 μg/25 μl i.a.) (intra-articular) 30 min before the carrageenan, reduced the oedema induced by the irritant by 45±3 and 48±5% (n=6) respectively, with a maximum inhibitory effect 6 hours after administration of the compounds.

The administration of dexamethasone (100 μg/25 μl i.a. 30 min before the carrageenan) reduced the oedema by 57±3%, whereas it proved inactive at 10 μg.

The co-administration of MEN16132 with dexamethasone (100 μg/25 μl i.a.) markedly boosted the anti-oedema effect, completely eliminating the knee swelling caused by carrageenan. Similar results were surprisingly observed even when the dose of dexamethasone was reduced ten-fold, to 10 μg/25 μl i.a.

The results of the effect of MEN16132 and dexamethasone for joint pain were qualitatively and quantitatively similar to those obtained with oedema. MEN16132 or dexamethasone 100 μg i.a. 30 min before the carrageenan reduced joint pain by 38±4% and 44±3% respectively, 6 hours after the irritant. Dexamethasone at 10 μg i.a. reduced pain by 14±4%. Co-administration of MEN16132 (100 μg i.a.) and dexamethasone, at 100 and 10 μg i.a., reduced joint pain by 92±2% and 91±2% respectively, with a significant boosting effect even at a dose of dexamethasone ten times lower.

Similarly surprising results were obtained on carrageenan-induced knee swelling in the rat with the association of MEN16132 and hydrocortisone, which is approximately 25 times less powerful than dexamethasone. MEN16132 at 100 μg i.a., administered 30 min before the carrageenan, reduced the knee swelling by 42±3% (n=6), whereas hydrocortisone at 100 μg i.a. proved practically inactive (−4±3%). Simultaneous administration of said two compounds reduced the swelling by 85±6%, confirming the strong boosting effect of the association between a bradykinin $B_2$ receptor antagonist and a cortisone, independently of its chemical structure.

In experimental models of inflammatory disorders of the airways (asthma, respiratory hyperreactivity induced by allergens or lipopolysaccharide), ophthalmic disorders (conjunctivitis caused by allergens, alkaline solutions and carrageenan) and dermatological disorders (allergic dermatitis), co-administration of kinin $B_2$ receptor antagonists and cortisones has produced results similar to those previously reported in arthritis of the knee, demonstrating an evident additive and synergic effect between the two classes of compound.

In the model of airway inflammation induced by lipopolysaccharide (LPS) in the guinea pig, the number of leucocytes collected by bronchoalveolar washing increased approximately tenfold compared with the control. Treatment with MEN16132 or icatibant (aerosol of a 1 mg/ml solution for 15 min) reduced by 6% and 5% respectively the number of inflammatory cells present in the airways after pre-treatment with LPS, while dexamethasone (aerosol of a 0.03 mg/ml solution for 15 min) reduced cell infiltration by 8%.

Co-administration of a kinin $B_2$ receptor antagonist (MEN16132 or icatibant) with dexamethasone, at the doses indicated above, inhibited by about 50% cell infiltration in the airways of the guinea pig caused by LPS with a marked, unexpected synergic effect between the two classes of compound.

Similar findings were obtained with an in vitro model, in cultures of human airway muscle cells stimulated for 24 hours with 1 μg/ml LPS, where an approximately 16-fold increase in the production of PGE2 was observed compared with the control.

MEN16132 or icatibant at 100 nM reduced LPS-induced release of PGE2 by 39% and 30% respectively, while dexamethasone (1 μM) reduced it by 45%. Combined treatment with a $B_2$ receptor antagonist (MEN16132 or icatibant) and dexamethasone abolished LPS-induced production of PGE2.

In this invention, especially in the description of compounds with a peptide structure, the following abbreviations have been used for some non-natural amino acids: Nal=naphthyl-alanine; NMePhe=N-methyl-phenylalanine, Oic=octahydroindol-2-carboxylic acid, Hyp=hydroxyproline, Igl=aminoindanecarboxylic acid, Cpg=1-aminocyclopentanecarboxylic acid, Tic=1,2,3,4-tetrahydroisoquinoline-3-carboxylic acid, F5F=pentafluorophenylalanine.

The invention claimed is:

1. A pharmaceutical composition comprising, a corticosteroid and a B2 kinin receptor antagonist, together with pharmaceutically acceptable carriers and excipients, wherein:
    a) the corticosteroid, either natural or synthetic, is selected from Cortisone, Hydrocortisone, Beclomethasone, Betamethasone, Budesonide, Dexamethasone, Flumethasone, Flunisolide, Fluocortone, Fluticasone, Methylprednisolone, Methylprednisone, Paramethasone, Prednisolone, and Triamcinolone; and
    b) the B2 kinin receptor antagonist is a compound of general formula (I):

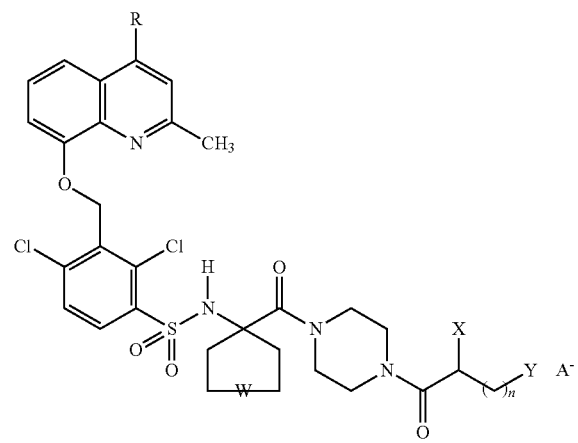

(I)

wherein
R is hydrogen or methyl;
W represents a single bond or an oxygen atom;
n is 3 or 4;
X is hydrogen or an amine group —NR1R2 wherein R1 and R2 are, independently from one another, hydrogen or a group selected from methyl, ethyl, n-propyl, and isopropyl;
Y is a quaternary ammonium —NR3R4R5 wherein R3, R4 and R5, independently from one another, are methyl, ethyl, n-propyl, isopropyl, butyl, isobutyl or n-pentyl;
A- is an anion formally derived from a pharmaceutically acceptable acid; and pharmaceutically acceptable salts, enantiomers and enantiomeric mixtures thereof.

2. A pharmaceutical composition according to claim 1, wherein said B2 kinin receptor antagonist is the compound (4-(S)-Amino-5-(4-{4-[2,4-dimethyl-quinolin-8-yloxymethyl)-benzenesulfonylamino]-tetrahydro-piran-4-carbonyl}-piperazin-1-yl)-5-oxo-pentyl]-trimethyl-ammonium as a salt with hydrochloric (MEN16132), acetic, sulfuric, trifluoroacetic, methanesulfonic, succinic or edetic acid.

3. A pharmaceutical composition according to claim 1, wherein the amount of corticosteroid per single dosage unit is 0.05-100 mg.

4. A pharmaceutical composition according to claim 1, wherein the amount of B2 kinin receptor antagonist per single dosage unit ranges from $6 \times 10^{-5}$ to $2 \times 10^{-2}$ millimoles, wherein if the B2 kinin receptor antagonist is MEN16132, the amount of MEN 16132 ranges from 0.05 to 17 mg per single unit dosage.

5. A pharmaceutical composition according to claim 1, which is in the form of an intra-articular or intrabursal injectable solution or in a transdermal form selected from cream, gel, transdermal bandage, eye drops, spray or aerosol solutions, and nasal spray.

6. A pharmaceutical composition according to claim 5, wherein the kinin antagonist is in the form of a crystalline, amorphous or lyophil solid, wherein said kinin antagonist is dissolved prior to use in a solution containing a corticosteroid to give an intra-articular or intrabursal injectable solution.

7. A pharmaceutical composition according to claim 1, further containing, a phosphate or citrate salt, sodium chloride, sodium edetate or a chelating agent.

8. A method for the prevention or treatment of articular inflammation, lesion and degeneration, said method comprising: administering an effective amount of a medicament comprising the combination of a corticosteroid and of a B2 kinin receptor antagonist according to claim 1 to a patient in need thereof; and preventing or treating said articular inflammation, lesion and degeneration of said patient.

9. A method for the prevention or treatment of allergic, non-allergic, chronic or acute respiratory tract inflammation, said method comprising:
administering an effective amount of a medicament comprising the combination of a corticosteroid and a B2 kinin receptor antagonist according to claim 1 to a patient in need thereof and; preventing or treating said allergic, non-allergic, chronic or acute respiratory tract inflammation of said patient.

10. The method of claim 8, wherein said B2 kinin receptor antagonist is MEN16132.

11. A pharmaceutical composition of claim 1, wherein said B2 kinin receptor antagonist is MEN16132.

12. A pharmaceutical composition according to claim 1, wherein the amount of corticosteroid per single dosage unit is 0.1-10 mg.

13. A pharmaceutical composition according to claim 1, wherein the amount of B2 kinin receptor antagonist per single dosage unit ranges from $1 \times 10^{-4}$ to $1 \times 10^{-2}$ millimoles wherein if the B2 kinin receptor antagonist is MEN16132 the amount of MEN16132 ranges from 0.09 to 9 mg per single unit dosage.

14. A pharmaceutical composition according to claim 1, wherein the amount of B2 kinin receptor antagonist per single dosage unit ranges from $3 \times 10^{-4}$ to $6 \times 10^{-3}$ millimoles wherein if the B2 kinin receptor antagonist is MEN16132 the amount of MEN16132 ranges from 0.26 to 5 mg per single unit dosage.

15. The method of claim 8, wherein said effective amount ranges between $3 \times 10^{-4}$ and $6 \times 10^{-3}$ millimoles B2 kinin receptor antagonist and between 0.01-10 mg corticosteroid.

16. The method of claim 8, wherein said articular inflammation, lesion and degeneration comprises: osteoarthritis and post-traumatic osteoarthritis, osteoarthrosis, spondylosis, synovitis, tenosynovitis, bursitis, contusion, distortion, dislocation and sub-dislocation, and osteochondrosis and dysplasias caused arthropathies.

17. The method of claim 9, wherein said respiratory tract inflammation comprises: asthma, rhinitis and obstructive chronic bronchopathy.

18. The method of claim 9, wherein said B2 kinin receptor antagonist is MEN16132.

* * * * *